United States Patent [19]

Andrews

[11] Patent Number: 4,469,686
[45] Date of Patent: Sep. 4, 1984

[54] SUBSTITUTED PHOSPHINIC ACIDS

[75] Inventor: Kenneth J. M. Andrews, Harpenden, England

[73] Assignee: Hoffmann-La Roche Inc., Nutley, N.J.

[21] Appl. No.: 229,912

[22] Filed: Jan. 30, 1981

[30] Foreign Application Priority Data

Feb. 1, 1980 [GB] United Kingdom ................ 8003420
Dec. 3, 1980 [GB] United Kingdom ................ 8038795

[51] Int. Cl.$^3$ .......................... A61K 33/42; C07F 9/65
[52] U.S. Cl. .................................... 424/200; 548/111; 260/502.4 R; 424/211
[58] Field of Search .......................... 548/111; 424/200

[56] References Cited

U.S. PATENT DOCUMENTS 4,147,780  4/1979  Dingwall et al. .................... 424/211

OTHER PUBLICATIONS

Derwent Soviet Inventions Illustrated, Section Ch: Chemical; Week C40 (1980); Pharmaceuticals, pp. 4 and 5.
Merck Index, 9th Edition (1976) p. 918.
Kudzin et al., Synthesis 12 (1980), pp. 1032–1034.

Primary Examiner—Richard Raymond
Attorney, Agent, or Firm—Jon S. Saxe; Bernard S. Leon; Matthew Boxer

[57] ABSTRACT

The invention is directed to substituted phosphinic and phosphonic acids, a process for the preparation thereof and the use thereof for the treatment of inflammatory conditions, degenerative joint diseases and Wilson's disease.

10 Claims, No Drawings

SUBSTITUTED PHOSPHINIC ACIDS

BACKGROUND OF THE INVENTION

The present invention relates to substituted phosphinic and phosphonic acids. More particularly, the invention is concerned with substituted phosphinic and phosphonic acids, a process for the preparation thereof, pharmaceutical preparations containing said derivatives and the use of said derivatives.

SUMMARY OF THE INVENTION

The substituted phosphinic and phosphonic acids provided by the present invention are compounds of the formula

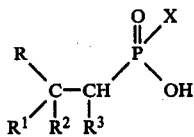   I wherein R is lower alkyl and $R^1$ is hydrogen or lower alkyl; or R and $R^1$ together with the carbon atom to which they are attached are a cycloalkane ring containing from 3 to 6 carbon atoms; $R^2$ is mercapto and $R^3$ is amino; or $R^2$ and $R^3$ together are a grouping of the formula

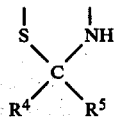

in which $R^4$ and $R^5$ each is lower alkyl; and X is hydrogen, hydroxy, lower alkyl or aryl,
and salts thereof.

It will be appreciated that formula I hereinbefore embraces compounds of the formula

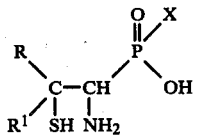   Ia wherein, R, $R^1$ and X are as above,
and compounds of the formula

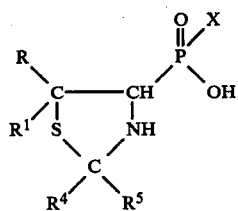   Ib wherein R, $R^1$, $R^4$, $R^5$ and X are as above.

DETAILED DESCRIPTION OF THE INVENTION

The term "lower alkyl" as used in this specification denotes a straight-chain or branched-chain alkyl group which preferably contains from 1 to 6 carbon atoms, for example, methyl, ethyl, propyl, isopropyl, butyl, isobutyl, tert. butyl, pentyl, hexyl, etc. Methyl is the preferred lower alkyl group. The phenyl group may be mentioned as an example of an aryl group.

Preferred compounds provided by the present invention are those in which R and $R^1$ each is lower alkyl.

Especially-preferred compounds of formula Ia is hereinbefore are:

DL-(1-amino-2-mercapto-2-methylpropyl)phosphinic acid,
DL-(1-amino-2-mercapto-2-methylpropyl)phosphonic acid and
DL-(1-amino-2-mercapto-2-methylpropyl)methylphosphinic acid.

Examples of other preferred compounds of formula Ia hereinbefore are:

DL-(1-amino-2-mercapto-2-methylpropyl)phenylphosphinic acid,
DL-(1-amino-2-mercapto-2-methylpropyl)butylphosphinic acid,
(−)-(1-amino-2-mercapto-2-methylpropyl)phosphinic acid and
(+)-(1-amino-2-mercapto-2-methylpropyl)phosphinic acid.

Especially-preferred compounds of formula Ib hereinbefore are:

DL-(2,2,5,5-tetramethyl-4-thiazolidinyl)phosphinic acid,
DL-(2,2,5,5-tetramethyl-4-thiazolidinyl)phosphonic acid and
DL-(2,2,5,5-tetramethyl-4-thiazolidinyl)methylphosphinic acid.

Examples of other preferred compounds of formula Ib hereinbefore are:

DL-(2,2,5,5-tetramethyl-4-thiazolidinyl)phenylphosphinic acid and
DL-(2,2,5,5-tetramethyl-4-thiazolidinyl)butylphosphinic acid.

According to the process provided by the present invention, the compounds of formula I hereinbefore and salts thereof are prepared by (a) for the preparation of an acid addition salt of a compound of formula Ib hereinbefore, reacting an acid addition salt of a compound of the formula

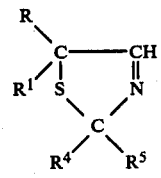   II wherein R, $R^1$, $R^4$ and $R^5$ are as above,
with an acid of the formula

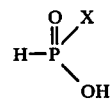   III wherein X is as above,
or (b) for the preparation of a compound of formula Ia hereinbefore or an acid addition salt thereof, cleaving the thiazolidine ring in a compound of formula Ib hereinbefore or in a compound of the formula

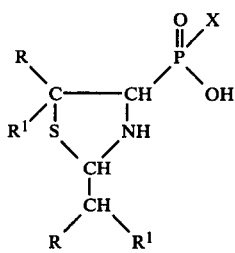

wherein R, R¹ and X are as above,
or in an acid addition salt of a compound of formula Ib or IV,
or (c) for the preparation of a compound of formula Ib hereinbefore, reacting a compound of formula Ia hereinbefore with a ketone of the formula

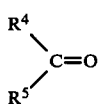

wherein R⁴ and R⁵ are as above,
or (d) if desired, separating a diastereoisomer mixture obtained into the diastereomer racemates, and/or (e) if desired, resolving a racemate obtained into the optical isomers, and/or (f) if desired, converting a compound of formula I into a salt or converting a salt of a compound of formula I into a compound of formula I.

According to embodiment (a) of the process, an acid addition salt of a compound of formula II is reacted with an acid of formula III to give an acid addition salt of a compound of formula Ib. It is preferred to use a hydrohalide, especially the hydrochloride, of a compound of formula II in this embodiment. The reaction can be carried out in the presence or absence of a solvent. For example, the reaction partners can be heated together to form a melt in the absence of a solvent. Alternatively, the reaction can be carried out in the presence of a suitable solvent, for example, an alkanol such as ethanol, at an elevated temperature, for example, at or near the boiling point of the mixture.

The cleavage of the thiazolidine ring in accordance with embodiment (b) of the process can be carried out according to generally-known methods. When a compound of formula Ib or an acid addition salt thereof is used, the cleavage can conveniently be carried out by heating a solution or suspension of said compound or salt in water, if desired in the presence of a concentrated hydrohalic acid, preferably concentrated hydrochloric acid. This heating is preferably carried out at the boiling point of the mixture. When a compound of formula IV or an acid addition salt thereof is used, the cleavage can conveniently be carried out by heating said compound or salt in the presence of water and a water-immiscible inert organic solvent with a carbonyl-binding compound, that is, a compound which is capable of reacting with the aldehyde liberated during the cleavage. Examples of such carbonyl-binding compounds are hydrazine, phenylhydrazine, 2,4-dinitrophenylhydrazine, semicarbazide, thiosemicarbazide or, preferably, hydroxylamine or a salt thereof, particularly hydroxylamine hydrochloride. Examples of water-immiscible organic solvents which can be used are aromatic hydrocarbons, for example, benzene, toluene, etc., or, preferably, halogenated hydrocarbons, for example, chloroform, chlorobenzene, etc. This cleavage method is advantageously carried out in the presence of a base such as an alkali metal hydroxide, for example, sodium hydroxide, and at the boiling point of the mixture. The desired product is isolated from the aqueous phase in a manner known per se, with the product of the reaction between the carbonyl-binding compound and the aldehyde being present in the organic phase.

The reaction of a compound of formula Ia with a ketone of formula V in accordance with embodiment (c) of the process to give a compound of formula Ib can be carried out in a manner known per se. Examples of ketones of formula V which can be used in this embodiment are acetone, ethyl methyl ketone, diethyl ketone, etc. Acetone is preferred.

The compounds of formula I contain an asymmetric centre and can therefore exist in racemic or optically-active form. Compounds of formula I which contain more than one asymmetric centre can exist in various diastereoisomeric forms. It will be appreciated that this invention includes within its scope all possible stereoisomers of the compounds of formula I and all possible diastereoisomer mixtures and racemates as well as the separation of diastereoisomer mixtures and the resolution of racemates which can be carried out according to methods known per se.

Compounds of formula I form salts with acids and with bases. Examples of salts formed with acids are hydrochlorides, hydrobromides, sulphates, nitrates, phosphates, methanesulphonates, ethanesulphonates, toluenesulphonates, acetates, oxalates, succinates, fumarates, maleates, malates, citrates, etc. Examples of salts formed with bases are sodium, potassium, lithium, calcium, ammonium and substituted-ammonium salts as well as salts formed with appropriate heterocyclic bases. The pharmaceutically-acceptable salts are preferred. The conversion of a compound of formula I into a salt can be carried out in a conventional manner. Likewise, conventional methods can be used for the conversion of a salt of a compound of formula I into a compound of formula I.

The compounds of formula II hereinbefore and their acid addition salts are either known or can be prepared in analogy to known substances.

The compounds of formula IV hereinbefore and their acid addition salts also form part of the present invention. They can be prepared by reacting an acid addition salt of a compound of the formula

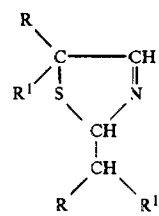

wherein R and R¹ are as above,
with an acid of formula III hereinbefore in a manner analogous to that described earlier in connection with embodiment (a) of the process provided by this invention and, if desired, converting the resulting acid addition salt of a compound of formula IV into a compound of formula IV.

The compounds of formula I hereinbefore and their pharmaceutically-acceptable salts possess valuable therapeutic properties. They can be used especially in the treatment of inflammatory conditions, degenerative joint diseases, for example, rheumatoid arthritis and osteoarthritis, and Wilson's disease.

In order to demonstrate the pharmacological activity of the compounds of formula I, the representative members listed below were subjected to the following tests:

Compound A: DL-(1-Amino-2-mercapto-2-methylpropyl)phosphonic acid.
Compound B: DL-(1-Amino-2-mercapto-2-methylpropyl)phosphinic acid.
Compound C: DL-2,2,5,5-Tetramethyl-4-thiazolidinyl)phosphonic acid.
Compound D: DL-(2,2,5,5-Tetramethyl-4-thiazolidinyl)phosphinic acid.

(A) Test for catalytic dismutation of superoxide:

This test is relevant to degenerative joint disease and inflammation. The method followed is the method of M. YOUNES and U. WESER [Biochem.Biophys.Res.-Commun. 1977, 78 (4) 1247–53] using a test compound: copper glycine ratio of 4:1. The results are compiled in Table I.

TABLE I

| Catalysis of superoxide dismutation | |
|---|---|
| Test compound | $I_{50}$ μM |
| A | 1.2 |
| B | 1.2 |

(B) Test for cupriuretic activity:

This test is relevant to Wilson's disease. The method followed is the method of K. GIBBS and J. M. WALSHE (Clinical Science and Molecular Medicine, 1977, 53, 317–20). The results are compiled in Table II.

TABLE II

| Cupriuretic activity at 1 mM/kg | |
|---|---|
| Test compound | % Increase |
| A | 139 |
| B | 397 |
| C | 122 |
| D | 308 |

Comparative toxicity:

Acute toxicity studies in mice have shown that the minimum single dose to cause death is >2400 mg/kg i.p. for compound B and ≦400 mg/kg i.p. for DL-penicillamine.

The compounds of formula I and their pharmaceutically-acceptable salts may be used as medicaments in the form of pharmaceutical preparations which contain them in association with a compatible pharmaceutical carrier material. This carrier material can be an organic or inorganic inert carrier material which is suitable for enteral, for example, oral, or parenteral administration, examples of such carrier materials being water, gelatin, talc, magnesium stearate, gum arabic, lactose, starches, vegetable oils, polyalkyleneglycols, petroleum jelly and the like. The pharmaceutical preparations can be made up in a solid form, for example, as tablets, dragées, suppositories or capsules, or in a liquid form, for example as solutions, suspensions or emulsions. The pharmaceutical preparations may be subjected to conventional pharmaceutical operations such as sterilization and/or may contain conventional pharmaceutical adjuvants such as preserving agents, stabilizing agents, emulsifying agents, wetting agents, flavoring agents, sweetening agents, coloring agents, salts for varying the osmotic pressure, buffers, etc. The pharmaceutical preparations can contain other therapeutically-active substances in addition to the compounds of formula I and their pharmaceutically-acceptable salts.

The compounds of formula I and their pharmaceutically-acceptable salts can be administered to adults in a daily dosage of from about 250 mg to about 2000 mg, the administration being effected in a single dosage or, preferably, in divided dosages. It will be appreciated that the foregoing dosage range is given by way of example only and that it can be varied upwards or downwards by the attending physician having regard to factors such as the nature and severity of the condition being treated, the particular compound of salt being administered, etc.

The following Examples illustrate the process provided by the present invention.

EXAMPLE 1

6.45 g of 2,2,5,5-tetramethyl-$\Delta^3$-thiazoline hydrochloride were mixed with 2.95 g (1 equivalent) of phosphorous acid and the mixture was heated to 100°–110° C., an exothermic reaction being initiated and the melt slowly solidifying. After 30 minutes, the mixture was cooled to room temperature and ethanol was added to give a suspension. The pH of the suspension was adjusted to 5–6 with propylene oxide. The precipitate was collected, washed with ethanol and diethyl ether and dried to give 6.0 g of DL-(2,2,5,5-tetramethyl-4-thiazolidinyl)phosphonic acid in the form of a white solid of melting point 235°–237° C. (decomposition).

The 2,2,5,5-tetramethyl-$\Delta^3$-thiazoline hydrochloride used as the starting material can be prepared as follows:

5.2 g of 2,2,5,5-tetramethyl-$\Delta^3$-thiazoline were dissolved in dry diethyl ether and the solution was cooled in an ice-bath. Dry hydrogen chloride was passed through the solution until the precipitation of solid was complete. The precipitate was collected, washed with diethyl ether and dried in a vacuum dessicator.

EXAMPLE 2

36.0 g of 2,2,5,5-tetramethyl-$\Delta^3$-thiazoline hydrochloride were dissolved in ethanol and 13.0 g (1 equivalent) of hypophosphorous acid were added. The solution was heated at 70° C. for 3 hours and filtered. The filtrate was cooled to room temperature, adjusted to pH 5 with propylene oxide and cooled at 0° C. for 4 hours. The solid was collected, washed with ethanol/diethyl ether and dried, there being obtained 34.0 g of DL-(2,2,5,5-tetramethyl-4-thiazolidinyl)phosphinic acid of melting point 191° C. (decomposition).

EXAMPLE 3

7.2 g of 2,2,5,5-tetramethyl-$\Delta^3$-thiazoline hydrochloride and 3.25 g (1 equivalent) of methylphosphinic acid were mixed thoroughly and the mixture was heated to 105°–110° C. and stirred. A melt formed and an acid gas was evolved. The melt slowly solidified and heating was continued for 10–15 minutes. The residue was treated with 3.0 g of propylene oxide in ethanol and the solution was left to stand for 12 hours. The solid was collected, washed with cold isopropanol/diethyl ether and dried. Recrystallization from isopropanol gave 2.1 g of DL-(2,2,5,5-tetramethyl-4-thiazolidinyl)methylphosphinic acid in the form of a white solid of melting point 193°–194° C.

EXAMPLE 4

2.0 g of DL-(2,2,5,5-tetramethyl-4-thiazolidinyl)phosphonic acid (prepared as described in Example 1) were dissolved in boiling water and the solution was concentrated by boiling off excess water until a crystalline solid began to separate. The mixture was cooled to 0° C. and the white crystals were collected. There was obtained 0.6 g of DL-(1-amino-2-mercapto-2-methylpropyl)phosphonic acid of melting point 242°–244° C. (decomposition).

EXAMPLE 5

0.5 g of DL-(2,2,5,5-tetramethyl-4-thiazolidinyl)phosphinic acid (prepared as described in Example 2) was dissolved in boiling water and the solution was concentrated by boiling. The solution was cooled to 0° C. and the white crystalline solid was collected. There was obtained 0.15 g of DL-(1-amino-2-mercapto-2-methylpropyl)phosphinic acid of melting point 205°–207° C. (decomposition).

EXAMPLE 6

1.0 g of DL-(2,2,5,5-tetramethyl-4-thiazolidinyl)methylphosphinic acid (prepared as described in Example 3) was dissolved in boiling water and the solution was boiled for 30 minutes and then concentrated. The solution was filtered and isopropanol was added to the filtrate. The crystalline product was collected, washed with isopropanol/diethyl ether and dried to give 0.7 g of DL-(1-amino-2-mercapto-2-methylpropyl)methylphosphinic acid in the form of a white solid of melting point 221° C.

EXAMPLE 7

0.54 g of 2,2,5,5-tetramethyl-$\Delta^3$-thiazoline hydrochloride and 0.42 g of phenylphosphinic acid in 10 ml of ethanol were heated to 70° C. for 2 hours. The mixture was cooled to room temperature and filtered. The residue was washed with ethanol and with diethyl ether and subsequently dried to give 0.65 g of DL-(2,2,5,5-tetramethyl-4-thiazolidinyl)phenylphosphinic acid hydrochloride of melting point 215°–217° C. (decomposition).

EXAMPLE 8

7.73 g of 2,2,5,5-tetramethyl-$\Delta^3$-thiazoline hydrochloride and 5.27 g of butylphosphinic acid were mixed together and the temperature was slowly increased to 100° C. The temperature rose to 130° C. on initiation of the reaction and heating was maintained for 0.5 hour. The resulting solid mixture was treated with methanol, the solid was collected, washed with methanol and recrystallized from methanol to give 5.66 g of DL-(2,2,5,5-tetramethyl-4-thiazolidinyl)butylphosphinic acid hydrochloride of melting point 204° C. (decomposition).

EXAMPLE 9

0.3 g of DL-(2,2,5,5-tetramethyl-4-thiazolidinyl)phenylphosphinic acid hydrochloride (prepared as described in Example 7) was suspended in boiling water and concentrated hydrochloric acid was added until a solution had formed. The solution was filtered and the filtrate was evaporated to dryness under reduced pressure. The solid residue was recrystallized from 3N hydrochloric acid to give DL-(1-amino-2-mercapto-2-methylpropyl)phenylphosphinic acid hydrochloride of melting point 190°–192° C. (decomposition).

EXAMPLE 10

7.7 g of DL-(2,2,5,5-tetramethyl-4-thiazolidinyl)butylphosphinic acid (prepared as described in Example 8) were suspended in 25 ml of water containing 5 ml of concentrated hydrochloric acid and the mixture was heated under reflux for 1 hour. The mixture was evaporated to dryness (once with ethanol) and the solid residue was recrystallized from a mixture of 20 ml of ethanol and 75 ml of diethyl ether. The crystalline product was collected, there being obtained 4.1 g of DL-(1-amino-2-mercapto-2-methylpropyl)butylphosphinic acid hydrochloride of melting point 159°–160° C. (decomposition).

EXAMPLE 11

2.23 g of racemic (2-isopropyl-5,5-dimethyl-4-thiazolidinyl)phosphinic acid and 0.77 g of hydroxylamine hydrochloride were dissolved in 15 ml of deoxygenated water containing 0.48 g of sodium hydroxide and 15 ml of chloroform were added. The mixture was heated under reflux for 1 hour, cooled to room temperature and 3 ml of concentrated hydrochloric acid were added. The chloroform layer was removed and the aqueous layer was extracted with two 15 ml portions of chloroform. The aqueous layer was filtered, evaporated to dryness (twice with ethanol) and the residue was suspended in 15 ml of ethanol and treated with 10 ml of acetone. The mixture was heated under reflux for 0.5 hour, cooled to room temperature and filtered. The filtrate was treated with 1.5 ml of propylene oxide. The mixture was cooled at 0°–5° C. for 2 hours. The resulting solid was collected, washed with isopropanol and dried, there being obtained 1.5 g of DL-(2,2,5,5-tetramethyl-4-thiazolidinyl)phosphinic acid of melting point 190° C. (decomposition).

The racemic (2-isopropyl-5,5-dimethyl-4-thiazolidinyl)phosphinic acid used as the starting material can be prepared as follows:

31.6 g of 2-isopropyl-5,5-dimethyl-$\Delta^3$-thiazoline were dissolved in 300 ml of dry diethyl ether and the solution was cooled in an ice-bath. Dry hydrogen chloride was passed through the solution until no further precipitation occurred. The solid was collected, washed with dry diethyl ether and dried to give 35 g of 2-isopropyl-5,5-dimethyl-$\Delta^3$-thiazoline hydrochloride.

19.4 g of 2-isopropyl-5,5-dimethyl-$\Delta^3$-thiazoline hydrochloride and 16.0 g of hypophosphorous acid were dissolved in 75 ml of ethanol and the solution was heated to 70° C. for 1 hour. The solution was cooled to room temperature and filtered. The filtrate was then treated with 7 ml of propylene oxide and the mixture was cooled at 0°–5° C. for 3 hours. The solid was collected, washed with ethanol and diethyl ether and dried. There were obtained 18.4 g of racemic (2-isopropyl-5,5-dimethyl-4-thiazolidinyl)phosphinic acid of melting point 200° C. (decomposition).

EXAMPLE 12

1.5 g of DL-(2,2,5,5-tetramethyl-4-thiazolidinyl)phosphinic acid were dissolved in 10 ml of boiling water and the volume was reduced by boiling for 0.25 hour. The mixture was cooled to room temperature and diluted with 25 ml of isopropanol. The resulting mixture was cooled at 0° C. overnight. The resulting solid was collected, washed with isopropanol and dried to give 0.85 g of DL-(1-amino-2-mercapto-2-methylpropyl)-phosphinic acid of melting point 211° C. (decomposition).

EXAMPLE 13

(a) 1.7 g of DL-(1-amino-2-mercapto-2-methylpropyl)phosphinic acid were dissolved in 50 ml of deoxygenated water containing 1.7 g of sodium bicarbonate. The solution was held at 0° C. under an argon atmosphere. 1.7 ml of benzyl chloroformate were added and the mixture was stirred for 2 hours, the temperature being allowed to rise to room temperature during this time. The mixture was extracted with 20 ml of diethyl ether and the aqueous layer was separated. The aqueous extract was cooled to 0° C. and acidified to pH 1 with 2N hydrochloric acid. The oil which separated slowly solidified and was recrystallized from ethyl acetate/petroleum ether. The resulting DL-(1-benzyloxycarbonylamino-2-mercapto-2-methylpropyl)phosphinic acid melted at 114°–120° C.

(b) 6.36 g of DL-(1-benzyloxycarbonylamino-2-mercapto-2-methylpropyl)phosphinic acid were dissolved in 20 ml of hot ethanol and the solution was treated with 2.52 g of (−)-α-methylbenzylamine in 5 ml of ethanol. The resulting solution was cooled slowly and the crystalline product was collected. There were obtained 1.60 g of the (−)-α-methylbenzylamine salt of (+)-(1-benzyloxycarbonylamino-2-mercapto-2-methylpropyl)-phosphinic acid of melting point 185°–189° C. and specific rotation $[\alpha]_D^{20} = +22.2°$ (c=1% in ethanol). The product was crystallized to constant rotation, namely $[\alpha]_D^{20} = +24.6°$ (c=1% in ethanol), and then had a melting point of 187°–189° C.

(c) The mother liquors from the crystallization of the (−)-α-methylbenzylamine salt in paragraph (b) were evaporated. The solid residue was suspended in water and acidified to pH 1 with 2N hydrochloric acid. The mixture was extracted with two 25 ml portions of diethyl ether and the combined ethereal extracts were dried over magnesium sulphate. After filtration and evaporation of the diethyl ether, the product was treated with (+)-α-methylbenzylamine in the same proportions as described in paragraph (b). There was obtained the crystalline (+)-α-methylbenzylamine salt of (−)-(1-benzyloxycarbonylamino-2-mercapto-2-methylpropyl)phosphinic acid which was recrystallized from ethanol to constant rotation, namely $[\alpha]_D^{20} = -23.9°$ (c=1% in ethanol), and then had a melting point of 187°–189° C.

(d) The (+)-α-methylbenzylamine salt of (−)-(1-benzyloxycarbonylamino-2-mercapto-2-methylpropyl)-phosphinic acid [paragraph (c)] was suspended in water, the suspension was acidified to pH 1 with 2N hydrochloric acid and extracted with two 25 ml portions of diethyl ether. The combined ethereal extracts were dried over magnesium sulphate. Removal of the solvent by evaporation gave an oil which was dissolved in 2 ml of glacial acetic acid and treated with 5 ml of 45% hydrogen bromide in acetic acid. The solution was stored at room temperature overnight. 200 ml of diethyl ether were added and the cloudy suspension was cooled at 0° C. for 2 hours. The ethereal layer was decanted off and the residue was dissolved in 15 ml of methanol. 10 ml of acetone were then added. The solution was heated under reflux for 1 hour, cooled and filtered. The filtrate was adjusted to pH 5 by adding propylene oxide. The acetone adduct crystallized out at 0° C. and was collected. The acetone adduct, which melted at 183°–185° C., was dissolved in 5 ml of boiling water, filtered and concentrated to 3 ml by boiling off excess water. 15 ml of isopropanol were added and the mixture was allowed to cool slowly to room temperature. The mixture was then cooled at 0° C. for 16 hours. The resulting crystalline solid was collected and dried, there being obtained (−)-(1-amino-2-mercapto-2-methylpropyl)phosphinic acid of melting point 211°–212° C. (decomposition; $[\alpha]_D^{25} = -4.5°$ (c=1.5% in water).

(e) The (−)-α-methylbenzylamine salt of (+)-(1-benzyloxycarbonylamino-2-mercapto-2-methylpropyl)-phosphinic acid [paragraph (b)] was treated in an analogous manner to that described in paragraph (d) to give (+)-(1-amino-2-mercapto-2-methylpropyl)phosphinic acid of melting point 215° C. (decomposition); $[\alpha]_D^{25} = +4.0°$ (c=1.5% in water).

The following Examples illustrate pharmaceutical preparations containing a compound of formula I as the active ingredient:

EXAMPLE A

Tablets can contain the following ingredients:

| Ingredient | Per tablet |
|---|---|
| Compound of formula I | 100.0 mg |
| Lactose | 298.0 mg |
| Maize starch | 80.0 mg |
| Magnesium stearate | 2.0 mg |
| Total weight | 480.0 mg |

EXAMPLE B

Tablets can contain the following ingredients:

| Ingredient | Per tablet |
|---|---|
| Compound of formula I | 250.0 mg |
| Lactose | 96.0 mg |
| Magnesium stearate | 4.0 mg |
| Maize starch | 75.0 mg |
| Hydroxypropylmethylcellulose | 25.0 mg |
| Total weight | 450.0 mg |

What is claimed is:

1. Compounds of the formula

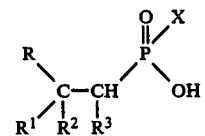

wherein R is lower alkyl and $R^1$ is hydrogen or lower alkyl;

or R and $R^1$ together with the carbon atom to which they are attached are a cycloalkane ring containing 3 to 6 carbon atoms; $R^2$ and $R^3$ together are a grouping of the formula

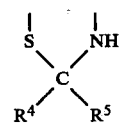

in which $R^4$ and $R^5$ each is lower alkyl; and X is hydrogen, lower alkyl or aryl, and salts thereof.

2. Compounds according to claim 1 wherein R is lower alkyl and $R^1$ is hydrogen or lower alkyl; or R and $R^1$ together are trimethylene, tetramethylene or pentamethylene.

3. Compounds according to claim 2 wherein R and $R^1$ each is lower alkyl.

4. A compound selected from the group consisting of: DL-(2,2,5,5-tetramethyl-4-thiazolidinyl)phenylphosphinic acid and
DL-(2,2,5,5-tetramethyl-4-thiazolidinyl)butylphosphinic acid.

5. DL-(2,2,5,5-tetramethyl-4-thiazolidinyl)phosphinic acid.

6. DL-(2,2,5,5-tetramethyl-4-thiazolidinyl)methylphosphinic acid.

7. Compounds of the formula

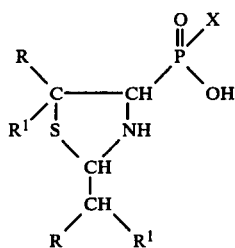

IV wherein R is lower alkyl and $R^1$ is hydrogen or lower alkyl; or R and $R^1$ together with the carbon atom to which they are attached are a cycloalkane ring containing from 3 to 6 carbon atoms; and X is hydrogen, lower alkyl or aryl, and acid addition salts thereof.

8. Racemic (2-isopropyl-5,5-dimethyl-4-thiazolidinyl)phosphinic acid.

9. A composition for the treatment of inflammatory conditions, degenerative joint diseases or Wilson's disease which comprises a compound of the formula

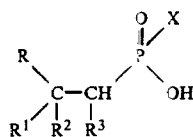

wherein R is lower alkyl and $R^1$ is hydrogen or lower alkyl; or R and $R^1$ together with the carbon atom to which they are attached are a cycloalkane ring containing from 3 to 6 carbon atoms; $R^2$ and $R^3$ together are a grouping of the formula

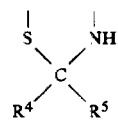

in which $R^4$ and $R^5$ each is lower alkyl; and X is hydrogen, lower alkyl or aryl, or a pharmaceutically-acceptable salt thereof and an inert carrier material.

10. A method for the treatment of inflammatory conditions, degenerative joint diseases or Wilson's disease which comprises administering an effective amount of a compound of the formula

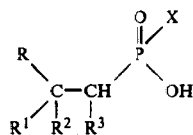

wherein R is lower alkyl and $R^1$ hydrogen or lower alkyl; or R and $R^1$ together with the carbon atom to which they are attached are a cycloalkane ring containing from 3 to 6 carbon atoms; $R^2$ and $R^3$ together are a grouping of the formula

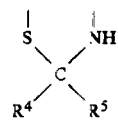

in which $R^4$ and $R^5$ each is lower alkyl; and X is hydrogen, lower alkyl or aryl or a pharmaceutically-acceptable salt thereof.

* * * * *